US012778542B2

(12) United States Patent
Mirar

(10) Patent No.: US 12,778,542 B2
(45) Date of Patent: Nov. 3, 2026

(54) SYSTEM FOR ADAPTIVE STRAIN IMAGING IN PATIENTS WITH ELEVATED HEART RATES

(71) Applicant: GE Precision Healthcare LLC, Waukesha, WI (US)

(72) Inventor: Hani Nozari Mirar, Oslo (NO)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 19/034,966

(22) Filed: Jan. 23, 2025

(65) Prior Publication Data

US 2026/0207164 A1 Jul. 23, 2026

(51) Int. Cl.
*A61B 8/00* (2006.01)
*A61B 8/08* (2006.01)

(52) U.S. Cl.
CPC ............ *A61B 8/0883* (2013.01); *A61B 8/465* (2013.01); *A61B 8/469* (2013.01)

(58) Field of Classification Search
CPC .................................................... A61B 8/0883
See application file for complete search history.

(56) References Cited

U.S. PATENT DOCUMENTS 8,396,268 B2 3/2013 Zabair et al.
11,763,456 B2 9/2023 Meyers et al.
2013/0066211 A1 3/2013 Konofagou et al.
2015/0183000 A1* 7/2015 Tai ...................... G01S 7/52017 367/7
2020/0214662 A1 7/2020 Konofagou et al.
2022/0192627 A1 6/2022 Quattrone-Brown et al.
2023/0316520 A1* 10/2023 Mirar ..................... G06V 20/70 382/100

FOREIGN PATENT DOCUMENTS

CN 118383797 A 7/2024
WO 2023113438 A1 6/2023

OTHER PUBLICATIONS

Effects of Frame Rate on Two-Dimensional Speckle Tracking Derived Measurements of Myocardial Deformation in Premature Infants, Echocardiography. May 2015 ; 32(5): 839-847.

(Continued)

*Primary Examiner* — Joseph M Santos Rodriguez
(74) *Attorney, Agent, or Firm* — SPQ IP LLC

(57) ABSTRACT

A strain imaging system may acquire first ultrasound data of a region of interest of a heart of a subject at a first frame rate during a first cardiac cycle of the heart of the subject. The strain imaging system may acquire second ultrasound data of a subset of the region of interest of the heart of the subject at a second frame rate during a second cardiac cycle of the heart of the subject. The strain imaging system may determine information related to cardiac deformation of the region of interest of the heart of the subject using strain imaging, the first ultrasound data, and the second ultrasound data. The strain imaging system may display the information related to cardiac deformation of the region of interest of the heart of the subject.

17 Claims, 12 Drawing Sheets

(56) References Cited

OTHER PUBLICATIONS

Guidelines for Performing a Comprehensive Pediatric Transthoracic Echocardiogram: Recommendations From the American Society of Echocardiography, Journal of the American Society of Echocardiography, (2024), 119-170, 37(2).
Strain and Strain Rate Imaging by Echocardiography—Basic Concepts and Clinical Applicability, Current Cardiology Reviews, May 2009; 5(2): 133-148.
Accuracy of speckle tracking in the context of stress echocardiography in short axis view: An in vitro validation study.

* cited by examiner

600

800

SYSTEM FOR ADAPTIVE STRAIN IMAGING IN PATIENTS WITH ELEVATED HEART RATES

TECHNICAL FIELD

The present disclosure relates to systems and methods for determining information related to cardiac deformation of a region of interest of the heart of the subject using strain imaging. More specifically, the present disclosure relates to systems and methods for performing strain imaging using first ultrasound data of the region of interest of the heart of the subject acquired at a first frame rate during a first cardiac cycle of the heart and second ultrasound data of a subset of the region of interest of the heart of the subject acquired at a second frame rate during a second cardiac cycle of the heart.

BACKGROUND

The cardiac cycle may refer to a sequence of events of the heart that result in the movement of blood through the heart and through the body as a whole. A single performance of the cardiac cycle may result in a single heartbeat. Generally, the cardiac cycle may include diastole and systole. Diastole may begin with the closing of the aortic valve and the closing of the pulmonary valve, and end with the closing of the mitral valve and the closing of the tricuspid valve. Systole may begin with the closing of the mitral valve and the closing of the tricuspid valve, and end with the closing of the aortic valve and the closing of the pulmonary valve. The myocardium contracts and relaxes during the cardiac cycle to facilitate blood circulation through the heart's chambers and valves. In diastole, the heart relaxes which allows blood to fill the atria and flow into the ventricles via the atrioventricular valves. During systole, the ventricles contract, the atrioventricular valves close to prevent back-flow, and the semilunar valves open to eject blood into the aorta and pulmonary artery. After contraction, the heart relaxes again which allows the cardiac cycle to repeat.

Strain imaging may refer to an imaging technique to evaluate myocardial deformation. Strain may refer to the change in cardiac length of the myocardium from end-diastole to end-systole. Strain imaging may be used for assessment of myocardial mechanics. For example, strain imaging may be used to detect cardiomyopathies, heart disease, myocardial dysfunction, or the like. For strain imaging using ultrasound data, a region of interest of the heart may be segmented into a set of myocardial segments in ultrasound data. The myocardial segments may be tracked during the cardiac cycle using a strain imaging technique (e.g., a template matching technique, an image registration technique, an artificial intelligence (AI) technique, or the like) and the ultrasound data. Strain values for the set of myocardial segments may be determined based on the tracking of the myocardial segments. For example, a strain curve, or "strain trace," that includes strain values for a myocardial segment over the cardiac cycle may be determined. Various relevant strain values (e.g., end-systolic strain, peak systolic strain, peak strain, etc.) may be determined from the strain curve.

In ultrasound imaging, a frame rate, or "temporal resolution," may refer to a number of frames acquired per time-frame. An ultrasound image is formed by sending and receiving sound waves. Since the speed of sound in biological material is limited, it takes time to construct a single image. Because the heart is a beating organ, the time spent forming a good quality image (spatial resolution) affects the capture of temporal information (frame rate).

Cardiac events occur more rapidly in subjects with elevated heart rates (e.g., subjects experiencing tachycardia, pediatric subjects, or the like). Consequently, acquisition of ultrasound data at a normal frame rate may lead to temporal undersampling for strain imaging. Due to undersampling, speckle patterns decorrelate during consecutive frames. Therefore, motion estimation via speckle tracking echocardiography may fail to accurately capture cardiac motion. However, due to the inherent trade-off between spatial resolution and temporal resolution, very high frame rates might not be capable of being achieved without compromising spatial resolution. This reduction in spatial resolution can adversely affect strain imaging performance.

Multibeat acquisition is an approach to increase temporal resolution without sacrificing spatial resolution. However, multibeat acquisition may introduce stitching artifacts that can affect motion estimation via speckle tracking.

SUMMARY

This summary introduces concepts that are described in more detail in the detailed description. It should not be used to identify essential features of the claimed subject matter, nor to limit the scope of the claimed subject matter.

In an aspect, a system may include a lens, an acoustic matching layer, an acoustic dematching layer, and a plurality of transducer elements; a memory configured to store instructions; and one or more processors configured to execute the instructions to: acquire first ultrasound data of a region of interest of a heart of a subject at a first frame rate during a first cardiac cycle of the heart of the subject; acquire second ultrasound data of a subset of the region of interest of the heart of the subject at a second frame rate during a second cardiac cycle of the heart of the subject; determine information related to cardiac deformation of the region of interest of the heart of the subject using strain imaging, the first ultrasound data, and the second ultrasound data; and display the information related to cardiac deformation of the region of interest of the heart of the subject.

In another aspect, a method may include acquiring first ultrasound data of a region of interest of a heart of a subject at a first frame rate during a first cardiac cycle of the heart of the subject; acquiring second ultrasound data of a subset of the region of interest of the heart of the subject at a second frame rate during a second cardiac cycle of the heart of the subject; determining information related to cardiac deformation of the region of interest of the heart of the subject using strain imaging, the first ultrasound data, and the second ultrasound data; and displaying the information related to cardiac deformation of the region of interest of the heart of the subject.

In yet another aspect, a non-transitory computer-readable medium may store instructions that, when executed by one or more processors, cause the one or more processors to: acquire first ultrasound data of a region of interest of a heart of a subject at a first frame rate during a first cardiac cycle of the heart of the subject; acquire second ultrasound data of a subset of the region of interest of the heart of the subject at a second frame rate during a second cardiac cycle of the heart of the subject; determine information related to cardiac deformation of the region of interest of the heart of the subject using strain imaging, the first ultrasound data, and the second ultrasound data; and display the information related to cardiac deformation of the region of interest of the heart of the subject.

DETAILED DESCRIPTION

As addressed above, acquisition of ultrasound data at a normal frame rate for subjects experiencing elevated heart rates may lead to temporal undersampling for strain imaging. Due to undersampling, speckle patterns decorrelate during consecutive frames. Therefore, motion estimation via speckle tracking echocardiography may fail to accurately capture cardiac motion, which adversely affects strain imaging performance.

The present disclosure provides an improvement to strain imaging by leveraging the fact that cardiac motion may be reconstructed from the motion of a few landmarks. These landmarks may be categorized into two main groups. The first group may be fast-moving structures (e.g., basal territories), and the second group may be slow-moving structures (e.g., apical territories). When the heart rate elevates, the embodiments herein may recover the motion of fast-moving landmarks by acquiring high-frame scans around these structures. Therefore, by automatically identifying and segmenting these regions during a first cycle of acquisition, and then performing a zoomed acquisition around the fast-moving structures on the next cycle, the embodiments herein may acquire a mixed scan of high frame rates and normal frame rates to accurately track both types of structures. The present disclosure improves the reliability of strain imaging in cases where the frame rate of an acquisition is not suitable for speckle tracking echocardiography, such as in subjects with elevated heart rates.

Figure 1:
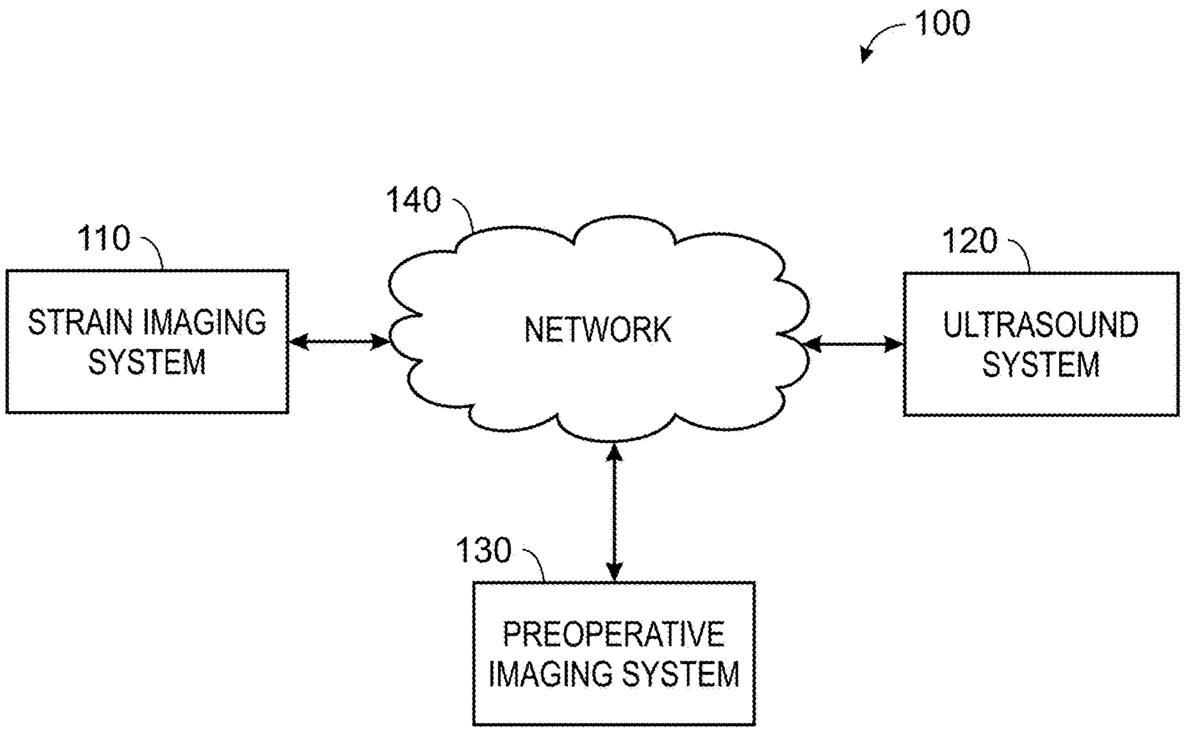
FIG. 1 is a diagram of an example system for determining information related to cardiac deformation of a region of interest of a heart of a subject using adaptive strain imaging.

FIG. 1 is a diagram of an example system for determining information related to cardiac deformation of a region of interest of a heart of a subject using adaptive strain imaging. As shown in FIG. 1, the system 100 may include a strain imaging system 110, an ultrasound system 120, a preoperative imaging system 130, and a network 140.

The strain imaging system 110 may be configured to acquire first ultrasound data of a region of interest of a heart of a subject at a first frame rate during a first cardiac cycle of the heart of the subject; acquire second ultrasound data of a subset of the region of interest of the heart of the subject at a second frame rate during a second cardiac cycle of the heart of the subject; determine information related to cardiac deformation of the region of interest of the heart of the subject using strain imaging, the first ultrasound data, and the second ultrasound data; and display the information related to cardiac deformation of the region of interest of the heart of the subject. For example, the strain imaging system 110 may be a computer, a server, a medical device, or the like.

The ultrasound system 120 may be configured to receive ultrasound data of a region of interest of a heart of a subject. For example, the ultrasound system 120 may be a two-dimensional (2D) ultrasound system, a three-dimensional (3D) ultrasound system, a four-dimensional (4D) ultrasound system, a Doppler ultrasound system, or the like. The subject may be a person, an animal, a phantom, or the like.

The preoperative imaging system 130 may be configured to receive preoperative imaging data of the region of interest of the heart of the subject. For example, the preoperative imaging system 130 may be a computed tomography (CT) system, a magnetic resonance imaging (MRI) system, an ultrasound system, an X-ray system, a positron emission tomography (PET) device, or the like.

The network 140 may permit communication between the strain imaging system 110, the ultrasound system 120, and the preoperative imaging system 130. For example, the network 140 may be a local area network (LAN), a wide area network (WAN), a metropolitan area network (MAN), a cellular network, a private network, an ad hoc network, an intranet, the Internet, a fiber optic-based network, a wired network, a wireless network, or the like, and/or a combination of these or other types of networks.

The number and arrangement of the system 100 are provided as an example. In practice, the system 100 may include additional systems, fewer systems, different systems, or differently arranged systems than those shown in FIG. 1. Additionally, or alternatively, a set of systems (e.g., one or more systems) of the system 100 may be integrated into a single system, and/or perform one or more functions described as being performed by another system, or set of systems, of the system 100.

Figure 2:
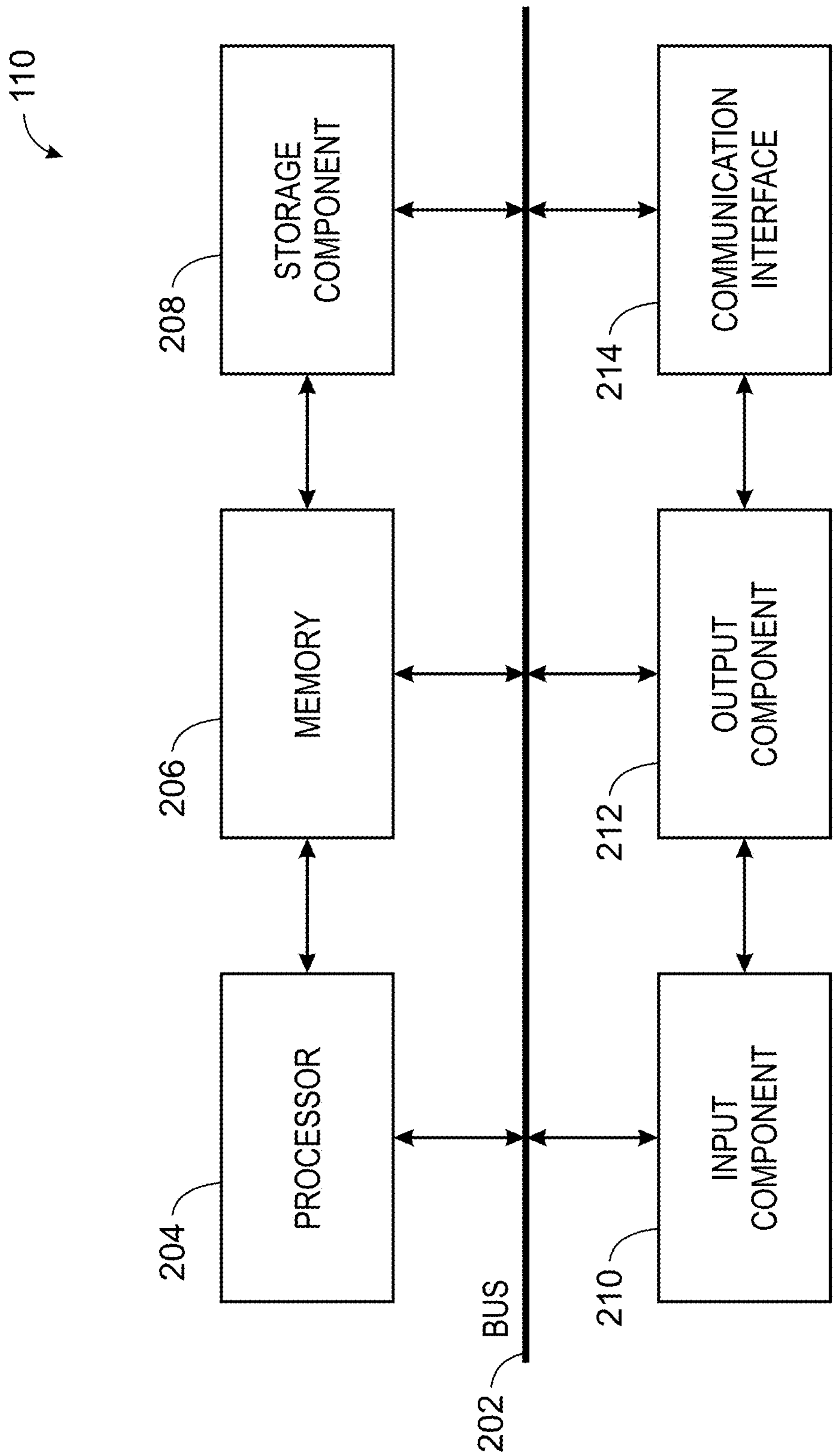
FIG. 2 is a diagram of an example deformation imaging system for determining information related to cardiac deformation of a region of interest of a heart of a subject using adaptive strain imaging.

FIG. 2 is a diagram of an example strain imaging system for determining information related to cardiac deformation of a region of interest of a heart of a subject using adaptive strain imaging. As shown in FIG. 2, the strain imaging system 110 may include a bus 202, a processor 204, a memory 206, a storage component 208, an input component 210, an output component 212, and a communication interface 214.

The bus 202 includes a component that permits communication among the components of the strain imaging system 110. The processor 204 may be implemented in hardware, firmware, or a combination of hardware and software. The processor 204 may be a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component.

The processor 204 may include one or more processors capable of being programmed to perform a function. The processor 204 may include one or more processors 204 configured to perform the operations described herein. For example, a single processor 204 may be configured to perform all of the operations described herein. Alternatively, multiple processors 204, collectively, may be configured to perform all of the operations described herein, and each of the multiple processors 204 may be configured to perform a subset of the operations described herein. For example, a first processor 204 may perform a first subset of the operations described herein, a second processor 204 may be configured to perform a second subset of the operations described herein, etc.

The memory 206 may include a random access memory (RAM), a read only memory (ROM), and/or another type of dynamic or static storage device (e.g., a flash memory, a magnetic memory, and/or an optical memory) that stores information and/or instructions for use by the processor 204.

The storage component 208 may store information and/or software related to the operation and use of the strain imaging system 110. For example, the storage component 208 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

The input component 210 may include a component that permits the strain imaging system 110 to receive information, such as via user input (e.g., a touch screen display, a keyboard, a keypad, a mouse, a button, a switch, a camera, and/or a microphone). Additionally, or alternatively, the input component 210 may include a sensor for sensing information (e.g., a global positioning system (GPS) component, an accelerometer, a gyroscope, and/or an actuator). The output component 212 may include a component that provides output information from the strain imaging system 110 (e.g., a display, a speaker for outputting sound at the output sound level, and/or one or more light-emitting diodes (LEDs)).

The communication interface 214 may include a transceiver-like component (e.g., a transceiver and/or a separate receiver and transmitter) that enables the strain imaging system 110 to communicate with other systems, such as via a wired connection, a wireless connection, or a combination of wired and wireless connections. The communication interface 214 may permit the strain imaging system 110 to receive information from another system and/or provide information to another system. For example, the communication interface 214 may include an Ethernet interface, an optical interface, a coaxial interface, an infrared interface, a radio frequency (RF) interface, a universal serial bus (USB) interface, a Wi-Fi interface, a cellular network interface, or the like.

The strain imaging system 110 may perform one or more processes described herein. The strain imaging system 110 may perform these processes based on the processor 204 executing software instructions stored by a non-transitory computer-readable medium, such as the memory 206 and/or the storage component 208. A computer-readable medium may be defined herein as a non-transitory memory device. A memory device may include memory space within a single physical storage device or memory space spread across multiple physical storage devices.

The software instructions may be read into the memory 206 and/or the storage component 208 from another computer-readable medium or from another system via the communication interface 214. When executed, the software instructions stored in the memory 206 and/or the storage component 208 may cause the processor 204 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of the components shown in FIG. 2 are provided as an example. In practice, the strain imaging system 110 may include additional components, fewer components, different components, or differently arranged components than those shown in FIG. 2. Additionally, or alternatively, a set of components (e.g., one or more components) of the strain imaging system 110 may perform one or more functions described as being performed by another set of components of the strain imaging system 110.

Figure 3:
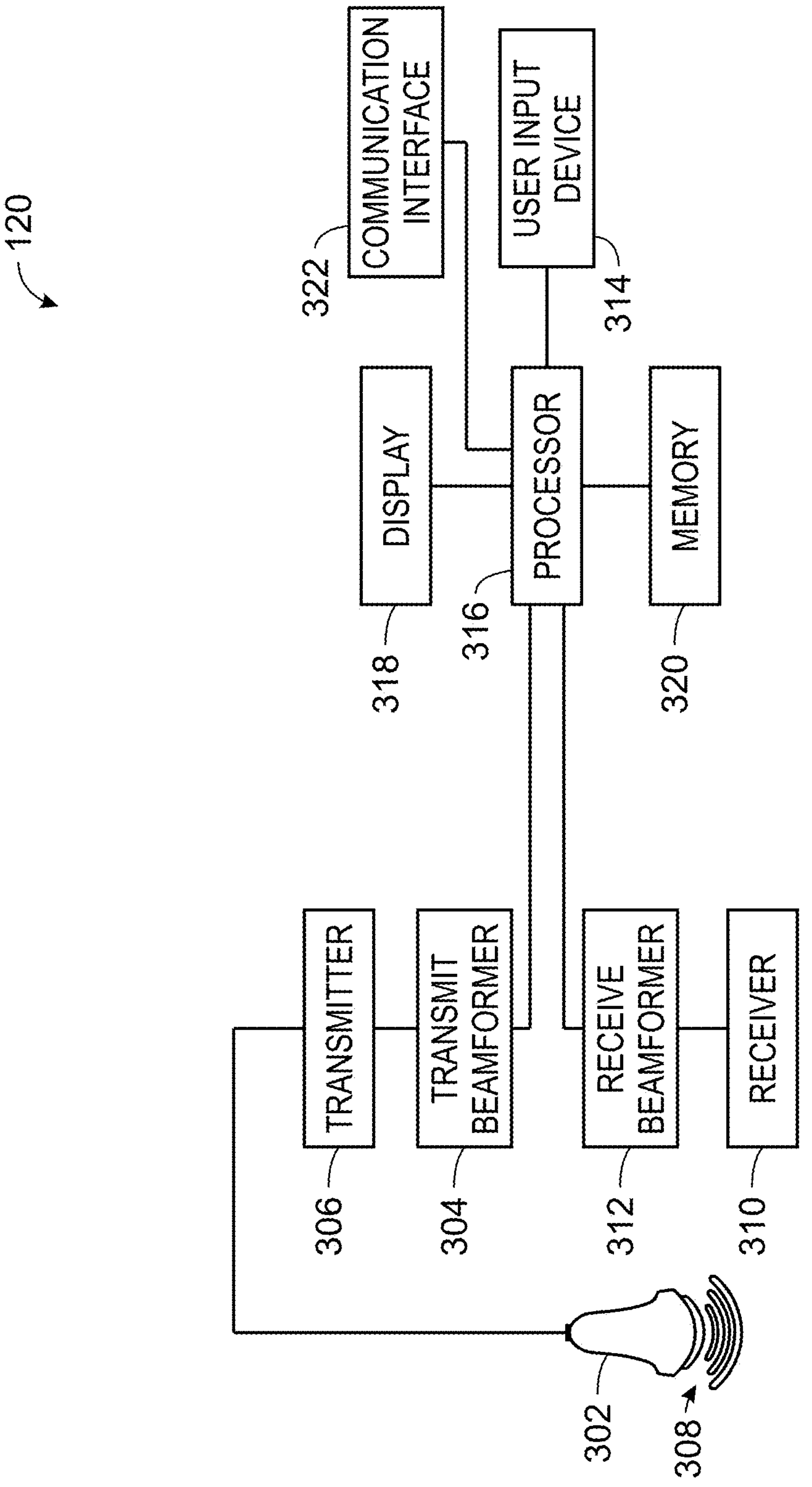
FIG. 3 is a diagram of an example ultrasound system for acquiring ultrasound data of the region of interest of the heart of the subject.

Is a diagram of an example ultrasound system for acquiring ultrasound data of the region of interest of the heart of the subject. As shown in FIG. 3, the ultrasound system 120 may include an ultrasound probe 302, a transmit beamformer 304, a transmitter 306, elements 308 a receiver 310, a receive beamformer 312, a user input device 314, a processor 316, a display 318, a memory 320, and a communication interface 322. The foregoing components may be connected via wired or wireless connections.

The ultrasound probe 302 may be configured to receive ultrasound data. For example, the ultrasound probe 302 may be a linear probe, a phase array probe, a curved linear probe coupled with a position tracking system, a mechanically steered linear array transducer, a phased array transducer, a curved linear array transducer, an electronically steered 2D transducer array, an electronic 3D (e3D) probe, an electronic 4d (e4D) probe, a low profile wearable patch version of any of the foregoing probes, or the like. According to an embodiment, the ultrasound probe 302 may be configured to generate ultrasound signals, emit the ultrasound signals towards the region of interest of a subject, receive echo ultrasound signals that are back-scattered from the region of interest of the subject, generate ultrasound data based on the echo ultrasound signals, and output the ultrasound data. The ultrasound probe 302 may include a lens, an acoustic matching layer, the transducer elements 308, an acoustic dematching layer, and a backing layer.

According to an embodiment, the lens may be configured to direct an ultrasound signal towards the region of interest of the subject. For example, the lens may be silicone, epoxy, rubber, or the like. According to an embodiment, the acoustic matching layer may be configured to facilitate matching of an impedance differential that may exist between the relatively high impedance transducer elements and the relatively low impedance subject. For example, the acoustic matching layer may be graphite, plastic, resin, or the like. According to an embodiment, the transducer elements 308, respectively, may be configured to receive an element specific transmit signal, transform the element specific transmit signal to an ultrasound signal, and transmit the ultrasound signal towards a region of interest. Additionally, or alternatively, the transducer elements 308 may be configured to receive an echo signal reflected by or backscattered from the region of interest, transform the echo signal to an electrical signal, and transmit the electrical signal. For example, the transducer elements 308 may be piezoelectric materials, such as $Pb(Mg_{1/3}Nb_{2/3})O_3$—$PbTiO_3$ ("PMN-PT"), $Pb(In_{1/2}Nb_{1/2})O_3$—$Pb(Mg_{1/3}Nb_{2/3})O_3$—$PbTiO_3$ ("PIN-PMN-PT"), Pb(ZrTi) ("PZT"), or the like. According to an embodiment, the acoustic dematching layer may be configured to decrease insertion losses and enhance a frequency bandwidth of the transducer elements 308. For example, the acoustic dematching layer may be tungsten carbide, silicon carbide, or the like. According to an embodiment, the backing layer may be configured to attenuate ultrasound signals directed from the transducer elements 308 in a direction opposite to the subject, and attenuate ultrasound signals deflected by a housing of the ultrasound probe 302. For example, the backing layer may be an epoxy, a metal, or the like.

The transmit beamformer 304 may be configured to apply delay times to electrical signals provided to the elements 308 to focus corresponding ultrasound signals at the region of interest. The transmitter 306 may be configured to transmit electrical signals to the elements 308 to drive the elements 308 to emit ultrasound signals towards the region of interest. The elements 308 may be configured to receive the electrical signals from the transmitter 306, convert the electrical signals into ultrasound signals, and emit the ultrasound signals towards the region of interest. The elements 308 may be configured to receive echo ultrasound signals that are back-scattered by the region of interest, convert the echo ultrasound signals into electrical signals, and provide the electrical signals to the receiver 310. The receiver 310 may be configured to receive electrical signals from the elements 308, and provide the electrical signals to the receive beamformer 312. The receive beamformer 312 may apply delay times to the electrical signals received from the elements 308.

The user input device 314 may be configured to receive a user input, and provide the user input to the processor 316. For example, the user input device 314 may be a touch screen display, a keyboard, a keypad, a mouse, a button, a switch, a microphone, or the like. Additionally, or alternatively, the user input device 314 may be configured to sense information. For example, the user input device 314 may sense information from an electro-magnetic positioning system, an inertial measurement system, an accelerometer, a gyroscope, an actuator, or the like.

The processor 316 may be configured to perform the operations as described herein. For example, the processor 316 may be a CPU, a GPU, an APU, a microprocessor, a microcontroller, a DSP, an FPGA, an ASIC, or another type of processing component. The processor 316 may be implemented in hardware, firmware, or a combination of hardware and software. The processor 316 may include one or more processors 316 configured to perform the operations described herein. For example, a single processor 316 may be configured to perform all of the operations described herein. Alternatively, multiple processors 316, collectively, may be configured to perform all of the operations described herein, and each of the multiple processors 316 may be configured to perform a subset of the operations described herein. For example, a first processor 316 may perform a first subset of the operations described herein, a second processor 316 may be configured to perform a second subset of the operations described herein, etc.

The processor 316 may be configured to control the ultrasound probe 302 to receive ultrasound data. The processor 316 may be configured to control which of the elements 308 are active, and control the shape of a beam emitted from the ultrasound probe 302. The processor 316 may generate ultrasound images for display. For example, the processor 316 may generate B-mode images, color Doppler images, anatomical M-mode images, color M-mode images, or the like. The ultrasound images may be 3D images, 2D images, single plane images, bi-plane images, three-plane images, multi-plane images, or the like. The ultrasound images may correspond to various anatomical planes (e.g., sagittal, coronal, and transverse) of the region of interest.

The display 318 may be configured to display information. For example, the display 318 may be a monitor, an LED display, a cathode ray tube, a projector display, a touchscreen, tablet computer, mobile phone, or the like. The display 318 may display ultrasound images based on the ultrasound data in real-time. For example, the display 318 may display the ultrasound images within one second, two seconds, five seconds, etc., of the ultrasound data being received by the ultrasound probe 302.

The memory 320 may be configured to store information and/or instructions for use by the processor 316. The memory 320 may be a non-transitory computer-readable medium. For example, the memory 320 may be a random access memory (RAM), a read only memory (ROM), and/or another type of dynamic or static storage device (e.g., a flash memory, a magnetic memory, and/or an optical memory) that stores information and/or instructions for use by the processor 316. The memory 320 may be configured to store instructions that, when executed by the processor 316, cause the processor 316 to perform the operations described herein.

The communication interface 322 may be configured to enable the processor 316 to communicate with other systems, such as via a wired connection, a wireless connection, or a combination of wired and wireless connections. For example, the communication interface 322 may include an Ethernet interface, an optical interface, a coaxial interface, an infrared interface, an RF interface, a USB interface, a Wi-Fi interface, a cellular network interface, or the like.

The number and arrangement of the components of the ultrasound system 120 shown in FIG. 3 are provided as an example. In practice, the ultrasound system 120 may include additional components, fewer components, different components, or differently arranged components than those shown in FIG. 3. Additionally, or alternatively, a set of components (e.g., one or more components) of the ultrasound system 120 may perform one or more functions described as being performed by another set of components of the ultrasound system 120.

Figure 4:
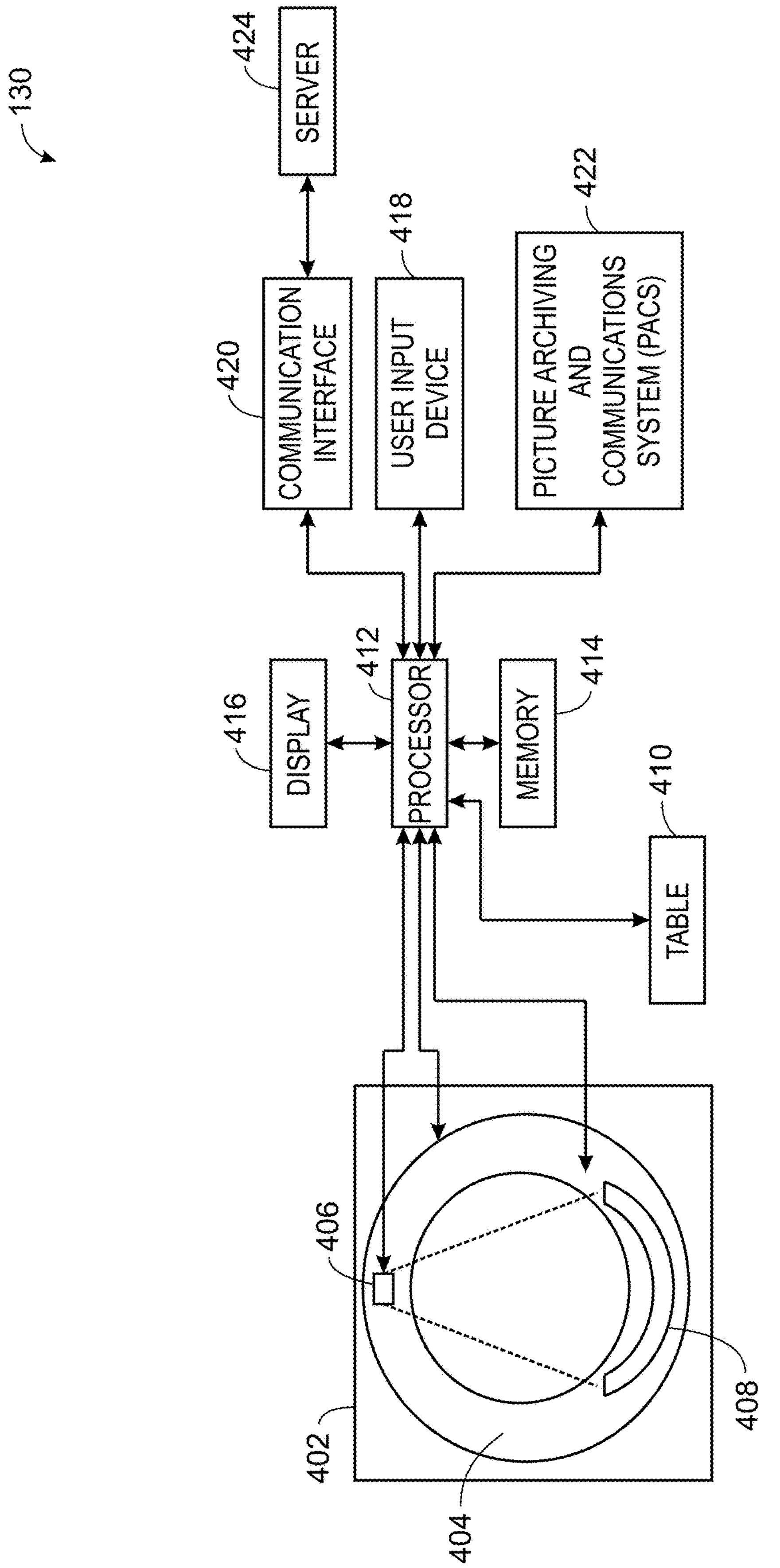
FIG. 4 is a diagram of an example preoperative imaging system for receiving preoperative imaging data of the region of interest of the heart of the subject.

FIG. 4 is a diagram of an example preoperative imaging system for receiving preoperative imaging data of the region of interest of the heart of the subject. As shown in FIG. 4, the preoperative imaging system 130 may include a gantry 402, a rotational frame 404, an X-ray source 406, an X-ray detector 408, a table 410, a processor 412, a memory 414, a display 416, a user input device 418, a communication interface 420, a picture archiving and communications system (PACS) 422, and a server 424.

The processor 412 may be configured to control operations of the preoperative imaging system 130. For example, the processor 412 may be a CPU, a GPU, an APU, a microprocessor, a microcontroller, a DSP, an FPGA, an ASIC, or the like. The processor 412 may be implemented in hardware, firmware, or a combination of hardware and software. The processor 412 may include one or more processors 412 configured to perform the operations described herein. For example, a single processor 412 may be configured to perform all of the operations described herein. Alternatively, multiple processors 412, collectively, may be configured to perform all of the operations described herein, and each of the multiple processors 412 may be configured to perform a subset of the operations described herein. For example, a first processor 412 may perform a first subset of the operations described herein, a second processor 412 may be configured to perform a second subset of the operations described herein, etc.

The processor 412 may be configured to control the gantry 402, movement of the rotational frame 404, the X-ray source 406, the X-ray detector 408, and movement of the table 410.

The memory 414 may be configured to store information and/or instructions for use by the processor 412. The memory 414 may be a non-transitory computer-readable medium. For example, the memory 414 may be a RAM, a ROM, a flash memory, a magnetic memory, an optical memory, or the like. The memory 414 may be configured to store instructions that, when executed by the processor 412, cause the processor 412 to perform the operations described herein.

The display 416 may be configured to display information. For example, the display 416 may be a monitor, an LED display, a cathode ray tube, a projector display, a touchscreen, tablet computer, mobile phone, or the like.

The user input device 418 may be configured to receive a user input, and provide the user input to the processor 412. For example, the user input device 418 may be a touch screen display, a keyboard, a keypad, a mouse, a button, a switch, a microphone, or the like. Additionally, or alternatively, the user input device 418 may be configured to sense information. For example, the user input device 418 may sense information from an electro-magnetic positioning system, an inertial measurement system, an accelerometer, a gyroscope, an actuator, or the like.

The communication interface 420 may be configured to enable the processor 412 to communicate with other devices, such as via a wired connection, a wireless connection, or a combination of wired and wireless connections. For example, the communication interface 420 may include an Ethernet interface, an optical interface, a coaxial interface, an infrared interface, an RF interface, a USB interface, a Wi-Fi interface, a cellular network interface, or the like. The PACS 422 may be configured to communicate with external systems and/or networks to permit users at various locations to access the medical image. The server 424 may be configured to store one or more models as described herein. For example, the server 424 may be an on-premises server, a cloud server, a virtual machine, or the like.

The number and arrangement of the components of the preoperative imaging system 130 shown in FIG. 4 are provided as an example. In practice, the preoperative imaging system 130 may include additional components, fewer components, different components, or differently arranged components than those shown in FIG. 4. Additionally, or alternatively, a set of components (e.g., one or more components) of the preoperative imaging system 130 may perform one or more functions described as being performed by another set of components of the preoperative imaging system 130.

Figure 5:
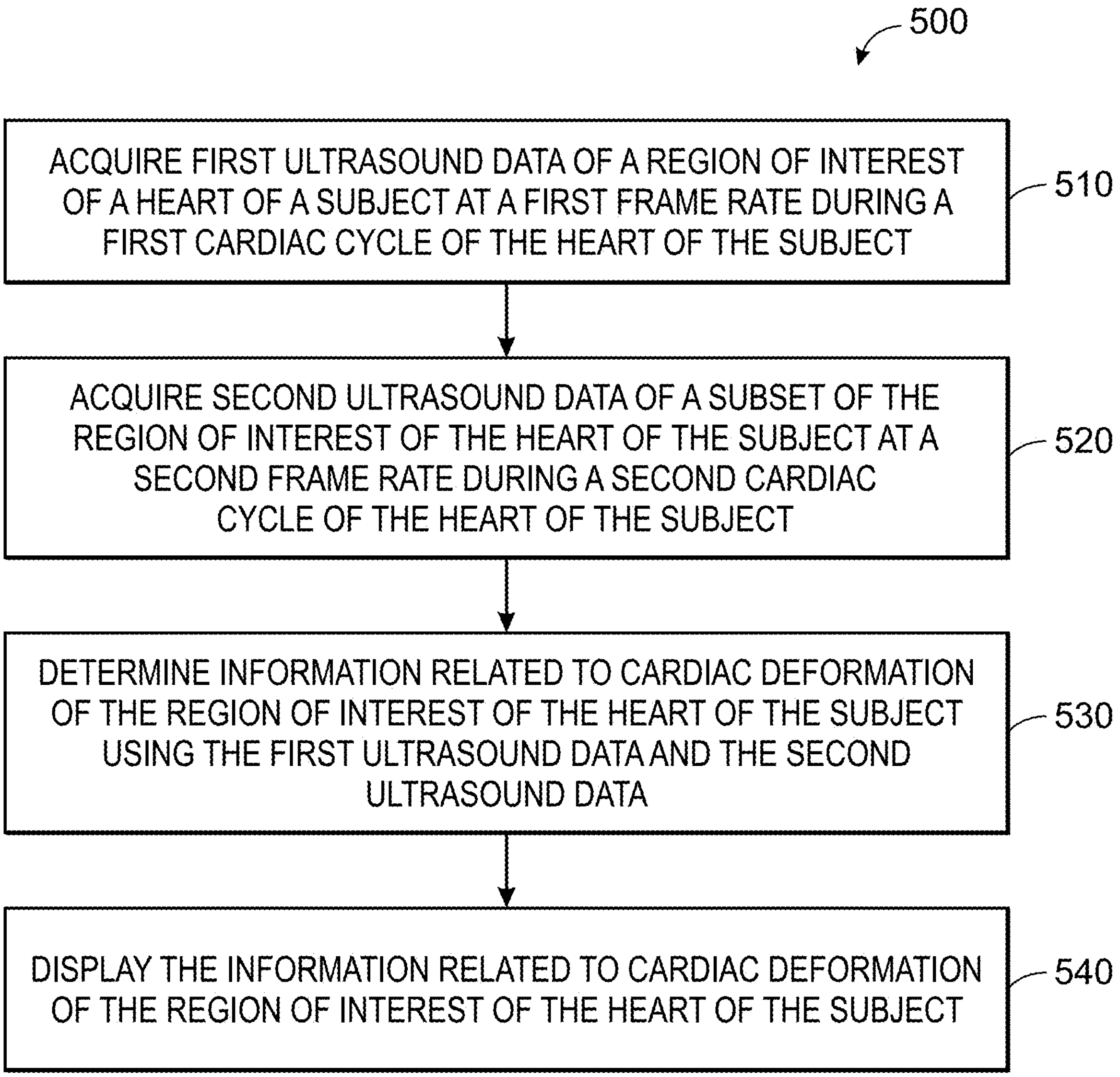
FIG. 5 is a flowchart of an example process for determining information related to cardiac deformation of a region of interest of a heart of a subject using adaptive strain imaging.

FIG. 5 is a flowchart of an example process 500 for determining information related to cardiac deformation of a region of interest of a heart of a subject using adaptive strain imaging. According to an embodiment, one or more operations of the process 500 may be performed by the strain imaging system 110. Additionally, or alternatively, one or more operations of the process 500 may be performed by the ultrasound system 120 and/or the preoperative imaging system 130.

As shown in FIG. 5, the process 500 may include acquiring first ultrasound data of a region of interest of a heart of a subject at a first frame rate during a first cardiac cycle of the heart of the subject (operation 510).

According to an embodiment, the region of interest may include one or more anatomical features of the heart, such as the left atrium, the left ventricle, the right atrium, the right ventricle, the mitral valve, the aortic valve, the pulmonary valve, the tricuspid valve, or the like. The subject may be a patient, an animal, a phantom, or the like. Although the embodiments herein are described in connection with cardiac structures, it should be understood that the embodiments herein are applicable to non-cardiac structures.

According to an embodiment, the first ultrasound data may correspond to the region of interest. For example, if the region of interest is the heart, then the first ultrasound data may depict the entire heart. As another example, if the region of interest is a specific chamber of the heart, then the first ultrasound data may depict the entire chamber.

According to an embodiment, the first ultrasound data may be acquired at a first frame rate. For example, the first frame rate may be any frame rate for acquisition of ultrasound data. As examples, the first frame rate may be fifty frames per second, fifty-five frames per second, sixty frames per second, or the like.

According to an embodiment, the first ultrasound data may be acquired during a first cardiac cycle of the heart of the subject. For example, the first cardiac cycle may be a specific cardiac cycle of the heart of the subject.

As further shown in FIG. 5, the process 500 may include acquiring second ultrasound data of a subset of the region of interest of the heart of the subject at a second frame rate during a second cardiac cycle of the heart of the subject (operation 520).

According to an embodiment, the subset of the region of interest may include one or more anatomical features of the heart, such as the left atrium, the left ventricle, the right atrium, the right ventricle, the mitral valve, the aortic valve, the pulmonary valve, the tricuspid valve, or the like. The subset of the region of interest may be a zoomed-in portion of the region of interest.

According to an embodiment, the second ultrasound data may correspond to the subset of the region of interest. For example, if the region of interest is the heart, then the second ultrasound data may depict less than the entire heart. As another example, if the region of interest is a specific chamber of the heart, then the first ultrasound data may depict less than the entire chamber.

According to an embodiment, the second ultrasound data may be acquired at a second frame rate. For example, the second frame rate may be any frame rate for acquisition of ultrasound data, and may be greater than the first frame rate. As examples, the second frame rate may be one hundred and fifty frames per second, one hundred and fifty-five frames per second, one hundred and sixty frames per second, or the like. Further, as another example, if the first frame rate is fifty frames per second, then the second frame rate may be one hundred and fifty frames per second.

According to an embodiment, the second ultrasound data may be acquired during a second cardiac cycle of the heart of the subject. For example, the second cardiac cycle may be a subsequent cardiac cycle of the heart of the subject as compared to the first cardiac cycle.

According to an embodiment, the strain imaging system 110 may determine the subset of the region of interest of the heart of the subject for which to acquire the second ultrasound data.

According to an embodiment, the strain imaging system 110 determine the subset of the region of interest of the heart of the subject for which to acquire the second ultrasound data based on the first ultrasound data. For example, the strain imaging system 110 may analyze the first ultrasound data of the region of interest of the heart of the subject, and determine the subset of the region of interest for which to acquire the second ultrasound data based on analyzing the first ultrasound data. According to an embodiment, the strain imaging system 110 may segment the region of interest of the heart into a set of myocardial segments, and track the respective segments during the first cardiac cycle. The strain imaging system 110 may determine motion characteristics of each of the myocardial segments, and determine the subset of the region of interest for which to acquire the second ultrasound data based on the motion characteristics. The motion characteristics may be displacement values, velocity values, or the like.

According to an embodiment, the strain imaging system 110 may determine the subset of the region of interest of the heart of the subject for which to acquire the second ultrasound data based on predetermined information. For example, the strain imaging system 110 may store predetermined information that delineates the subset of the region of interest, and may determine the subset of the region of interest for which to acquire the second ultrasound data based on the delineation of the subset of the region of interest.

According to an embodiment, the strain imaging system 110 may determine the subset of the region of interest of the heart of the subject for which to acquire the second ultrasound data based on an output of an artificial intelligence (AI) model. For example, the strain imaging system 110 may input the first ultrasound data into the AI model, and determine the subset of the region of interest for which to acquire the second ultrasound data based on an output of the AI model. The AI model may be a convolutional neural network (CNN), a residual neural network, a random forest model, a decision tree model, an artificial neural network (ANN), a Naïve Bayes model, a decision tree, a recurrent neural network (RNN), a logistic regression model, a support vector machine, or the like.

As further shown in FIG. 5, the process 500 may include determining information related to cardiac deformation of the region of interest of the heart of the subject using strain imaging, the first ultrasound data, and the second ultrasound data.

The strain imaging system 110 may generate an aggregated ultrasound data set based on the first ultrasound data and the second ultrasound data. For example, the strain imaging system 110 may register the first ultrasound data and the second ultrasound data such that the positions of the myocardial segments in the second ultrasound data correspond to the positions in the first ultrasound data.

To perform strain imaging, and according to an embodiment, the strain imaging system 110 may segment the region of interest of the heart into a set of myocardial segments, and track the respective segments over time using strain imaging and the aggregated ultrasound data set. Further, the strain imaging system 110 may determine respective strain values of the set of myocardial segments over time based on tracking the respective segments using strain imaging. For example, the strain imaging system 110 may determine a strain value based on a starting length of a segment and a final length of the segment. As an example, if the starting length of the segment is "10" and the final length of the segment is "8," then the strain imaging system 110 may determine a strain value of "−20%." As another example, if the starting length of the segment is "8" and the final length of the segment is "10," then the strain imaging system 110 may determine a strain value of "20%." The strain imaging system 110 may generate respective strain curves for the set of myocardial segments.

According to an embodiment, the information related to cardiac deformation of the region of interest of the heart of the subject may be strain values of myocardial segments of the heart, amounts of time to reach maximum strain values of the respective myocardial segments, particular myocardial segments that are associated with amounts of time that are greater than or less than respective thresholds, a mechanical dispersion value, a cardiac mechanical dyssynchrony parameter, or the like. Additionally, or alternatively, the information related to cardiac deformation of the region of interest heart of the subject may include an end-systolic strain that corresponds to a strain value at end-systole, peak systolic strain that corresponds to a peak strain value during systole, positive peak systolic strain that corresponds to a local myocardial stretching, a peak strain that corresponds to a peak strain value during the entire cardiac cycle, or the like. Additionally, or alternatively, the information related to cardiac deformation of the region of interest of the heart of the subject may be a velocity, a displacement, a strain rate, or the like, of a myocardial segment.

As further shown in FIG. 5, the process 500 may include displaying the information related to cardiac deformation of the region of interest of the heart of the subject For example, the strain imaging system 110 may display the information related to cardiac deformation of the anatomical feature of the heart, such as the mechanical dispersion value, strain values of the set of segments, amounts of time to reach maximum strain values of the respective segments, particular segments that are associated with amounts of time that are greater than or less than respective thresholds, or the like.

Although FIG. 5 describes the acquisition of first ultrasound data during a first cardiac cycle and the acquisition of second ultrasound data during a second cardiac cycle, it should be understood that the embodiments herein are applicable to the acquisition of n ultrasound data during n cardiac cycles using n, or m, frame rates. For example, the strain imaging system 110 may acquire ultrasound data corresponding to various subsets of the region of interest using various frame rates.

Figure 6:
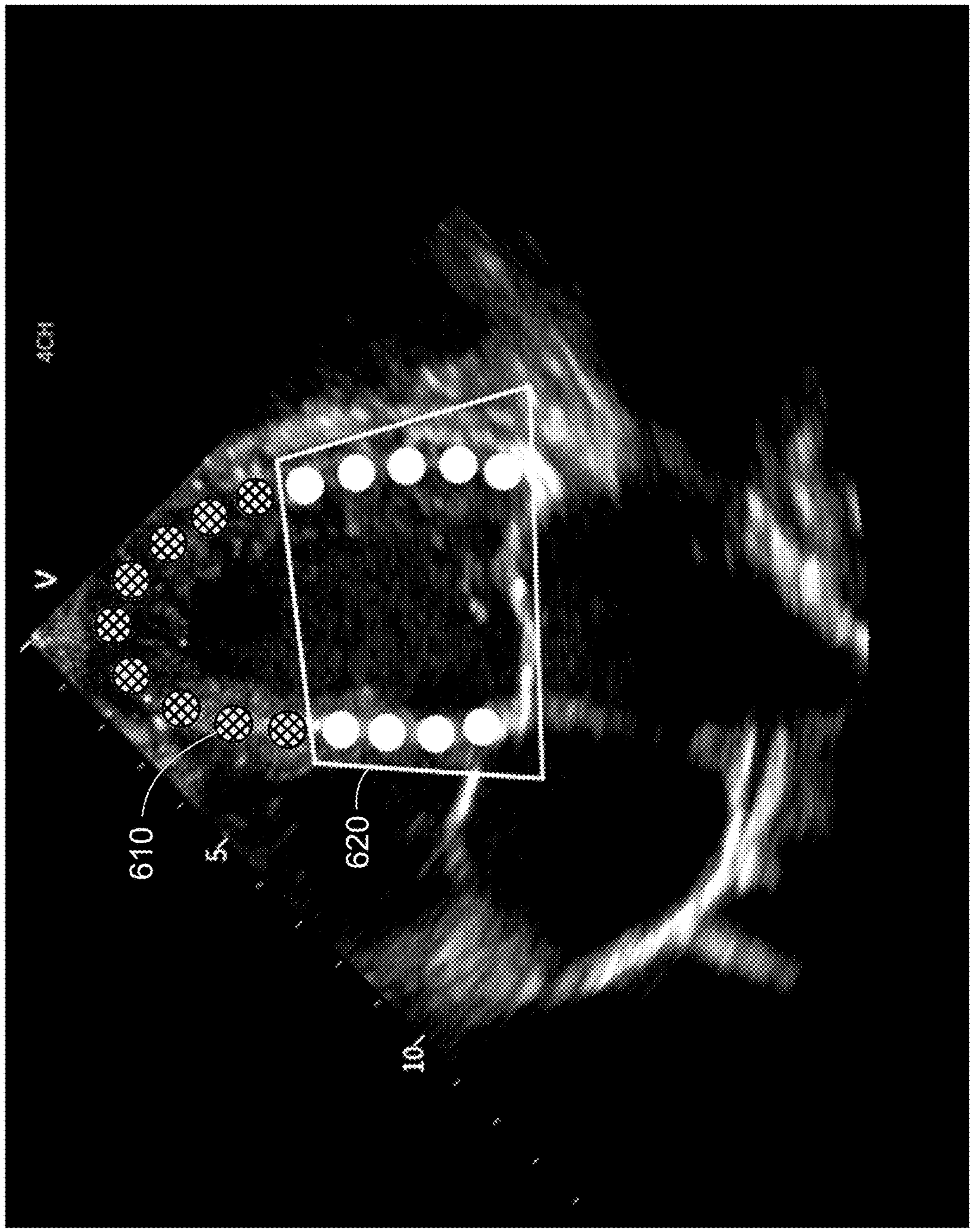
FIG. 6 is a diagram of an example region of interest and a subset of the region of interest.

FIG. 6 is a diagram 600 of an example region of interest and a subset of the region of interest. As shown in FIG. 6, the strain imaging system 110 may acquire ultrasound data of a region of interest which corresponds to the left ventricle of the heart of a subject. The region of interest of the heart of the subject includes a first subset 610 and a second subset 620. The first subset 610 corresponds to an apical portion of the left ventricle and may be associated with relatively less motion over the cardiac cycle, whereas the second subset 620 corresponds to a basal portion of the left ventricle and may be associated with relatively more motion over the cardiac cycle. The strain imaging system 110 may acquire first ultrasound data of the region of interest of the heart of a subject at a first frame rate during a first cardiac cycle of the heart of the subject. For example, the strain imaging system 110 may acquire first ultrasound data that depicts the first subset 610 and the second subset 620 during the first cardiac cycle of the heart of the subject. The strain imaging system 110 may acquire second ultrasound data of a subset of the region of interest of the heart of the subject at a second frame rate during a second cardiac cycle of the heart of the subject. For example, the strain imaging system 110 may acquire second ultrasound data that depicts the second subset 620 and that does not depict the first subset 610. In this way, the second ultrasound data is zoomed-in on the second subset 620, and may be acquired at a greater frame rate than as compared to the acquisition of the first ultrasound data in order to capture the increased motion of the second subset 620.

Figure 7:
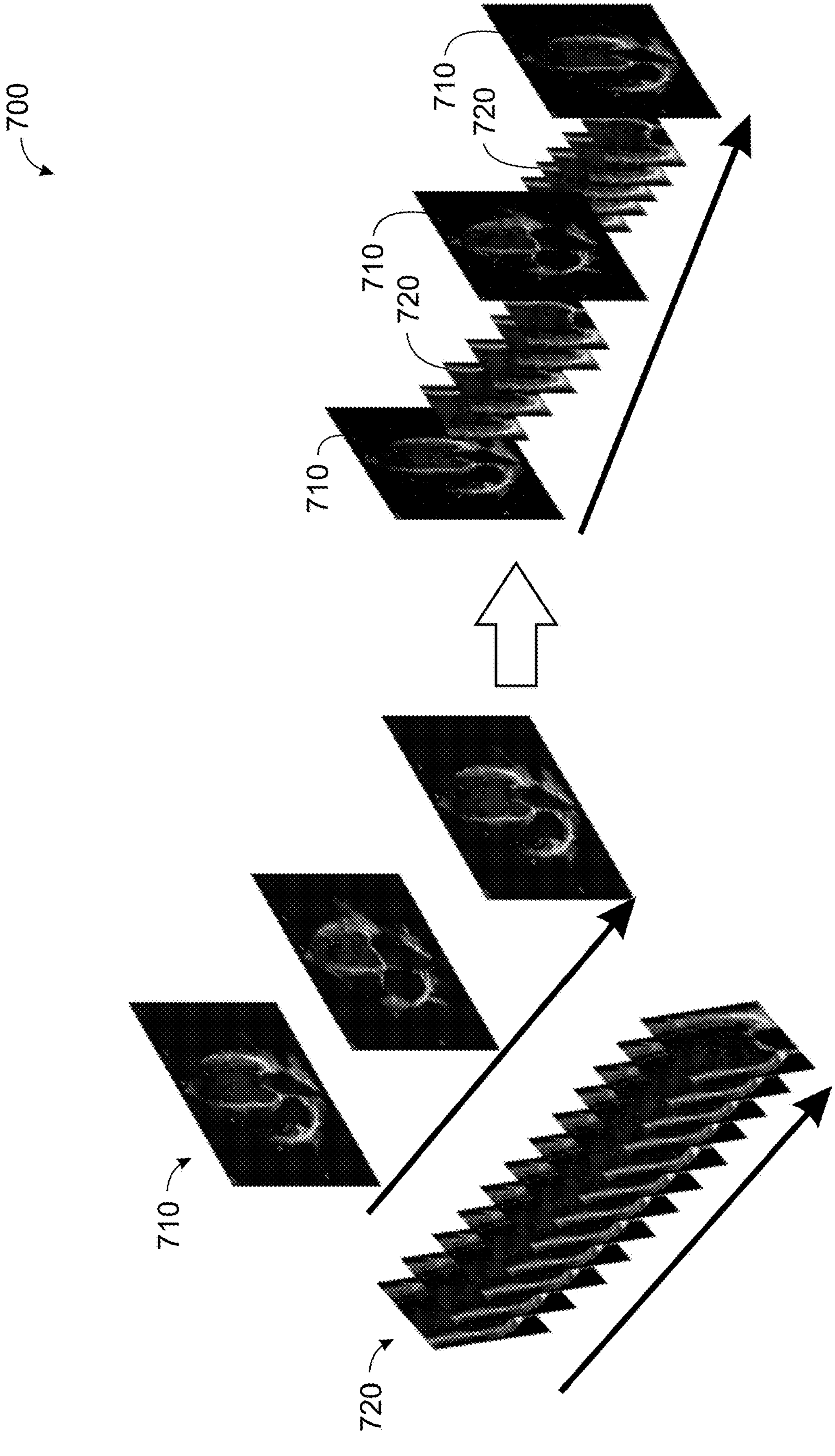
FIG. 7 is a diagram of examples first ultrasound data, second ultrasound data, and an aggregated ultrasound data set.

FIG. 7 is a diagram 700 of examples first ultrasound data, second ultrasound data, and an aggregated ultrasound data set. As shown in FIG. 7, the strain imaging system 110 may acquire ultrasound data of a region of interest which corresponds to the left ventricle of the heart of a subject. The region of interest of the heart of the subject includes a first subset and a second subset. The first subset corresponds to an apical portion of the left ventricle and may be associated with relatively less motion over the cardiac cycle, whereas the second subset corresponds to a basal portion of the left ventricle and may be associated with relatively more motion over the cardiac cycle. The strain imaging system 110 may acquire first ultrasound data 710 of the region of interest of the heart of a subject at a first frame rate during a first cardiac cycle of the heart of the subject. For example, the strain imaging system 110 may acquire first ultrasound data 710 that depicts the first subset and the second subset during the first cardiac cycle of the heart of the subject. The strain imaging system 110 may acquire second ultrasound data 720 of a subset of the region of interest of the heart of the subject at a second frame rate during a second cardiac cycle of the heart of the subject. For example, the strain imaging system 110 may acquire second ultrasound data 720 that depicts the second subset and that does not depict the first subset. In this way, the second ultrasound data 720 is zoomed-in on the second subset, and may be acquired at a greater frame rate than as compared to the acquisition of the first ultrasound data 710 in order to capture the increased motion of the second subset. Further, in this way, the second ultrasound data 720 may include a greater number of images than as compared to the first ultrasound data 710. The strain imaging system 110 may generate an aggregated ultrasound data set 730 that includes the first ultrasound data 710 and the second ultrasound data 720. For example, the strain imaging system 110 may register the first ultrasound data 710 and the second ultrasound data 720 such that the positions of the myocardial segments in the second ultrasound data correspond to the positions in the first ultrasound data 710.

Figure 8:
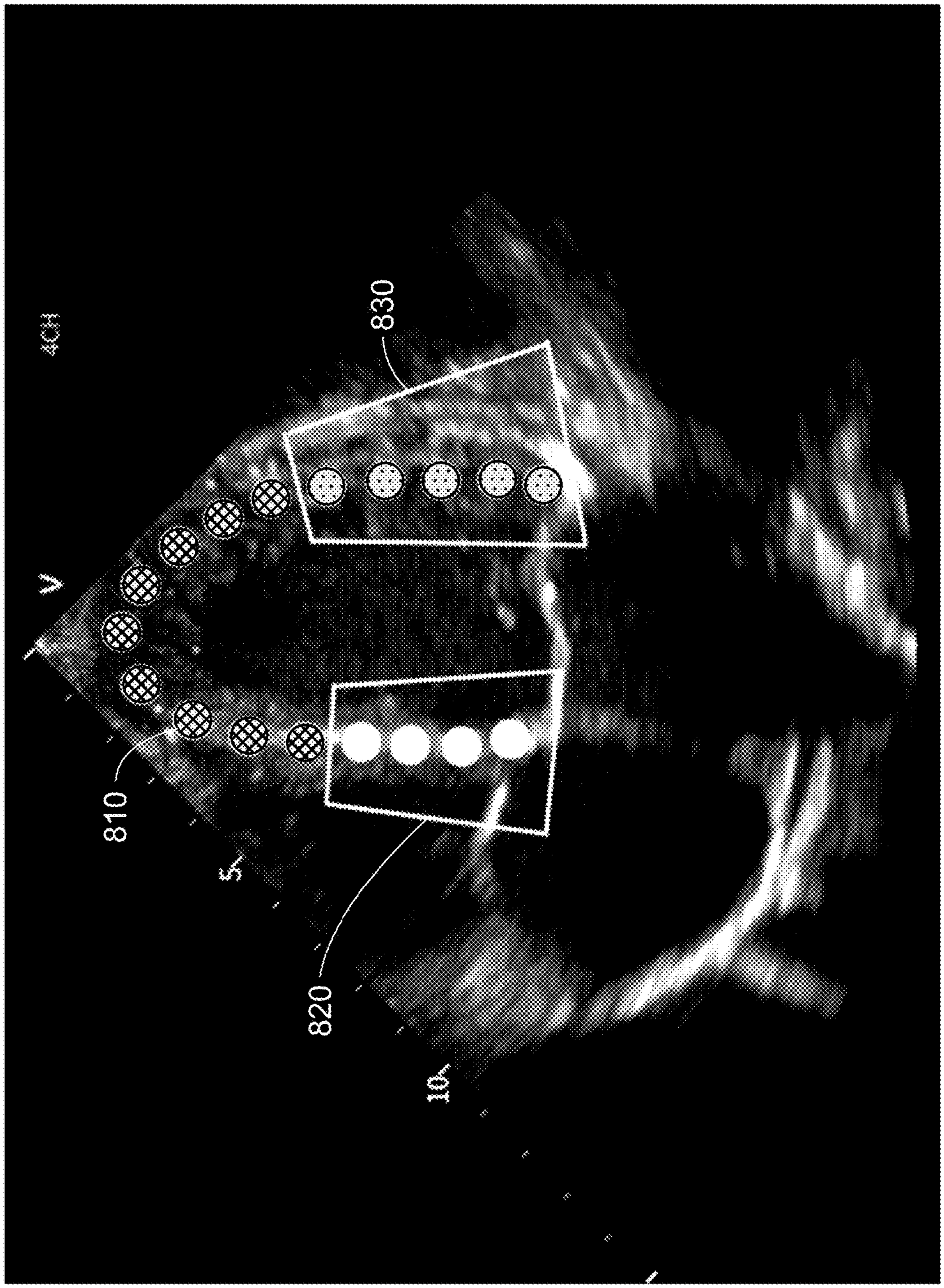
FIG. 8 is a diagram of an example region of interest, a first subset of the region of interest, and a second subset of the region of interest.

FIG. 8 is a diagram 800 of an example region of interest, a first subset of the region of interest, and a second subset of the region of interest. As shown in FIG. 8, the strain imaging system 110 may acquire ultrasound data of a region of interest which corresponds to the left ventricle of the heart of a subject. The region of interest of the heart of the subject includes a first subset 810, a second subset 820, and a third subset 830. The first subset 810 corresponds to an apical portion of the left ventricle and may be associated with relatively less motion over the cardiac cycle, whereas the second subset 820 corresponds to a left basal portion of the left ventricle and the third subset 830 corresponds to a right basal portion of the left ventricle which may each be associated with relatively more motion over the cardiac cycle than as compared to the first subset 810. The strain imaging system 110 may acquire first ultrasound data of the region of interest of the heart of a subject at a first frame rate during a first cardiac cycle of the heart of the subject. For example, the strain imaging system 110 may acquire first ultrasound data that depicts the first subset 810, the second subset 820, and the third subset 830 during the first cardiac cycle of the heart of the subject. The strain imaging system 110 may acquire second ultrasound data of a subset of the region of interest of the heart of the subject at a second frame rate during a second cardiac cycle of the heart of the subject. For example, the strain imaging system 110 may acquire second ultrasound data that depicts the second subset 820 and that does not depict the first subset 810 and the third subset 830. The strain imaging system 110 may acquire third ultrasound data of a subset of the region of interest of the heart of the subject at a third frame rate during a third cardiac cycle of the heart of the subject. For example, the strain imaging system 110 may acquire third ultrasound data that depicts the third subset 830 and that does not depict the first subset 810 and the second subset 820. The third frame rate may be the same as the second frame rate or may be different than the second frame rate. However, in any event, the third frame rate and the second frame rate may each be greater than the first frame rate. In this way, the second ultrasound data and the third ultrasound data are each respectively zoomed-in on the second subset 820 and the third subset 830, and may be acquired at a greater frame rate than as compared to the acquisition of the first ultrasound data in order to capture the increased motion of the second subset 820 and the third subset 830.

Figure 9:
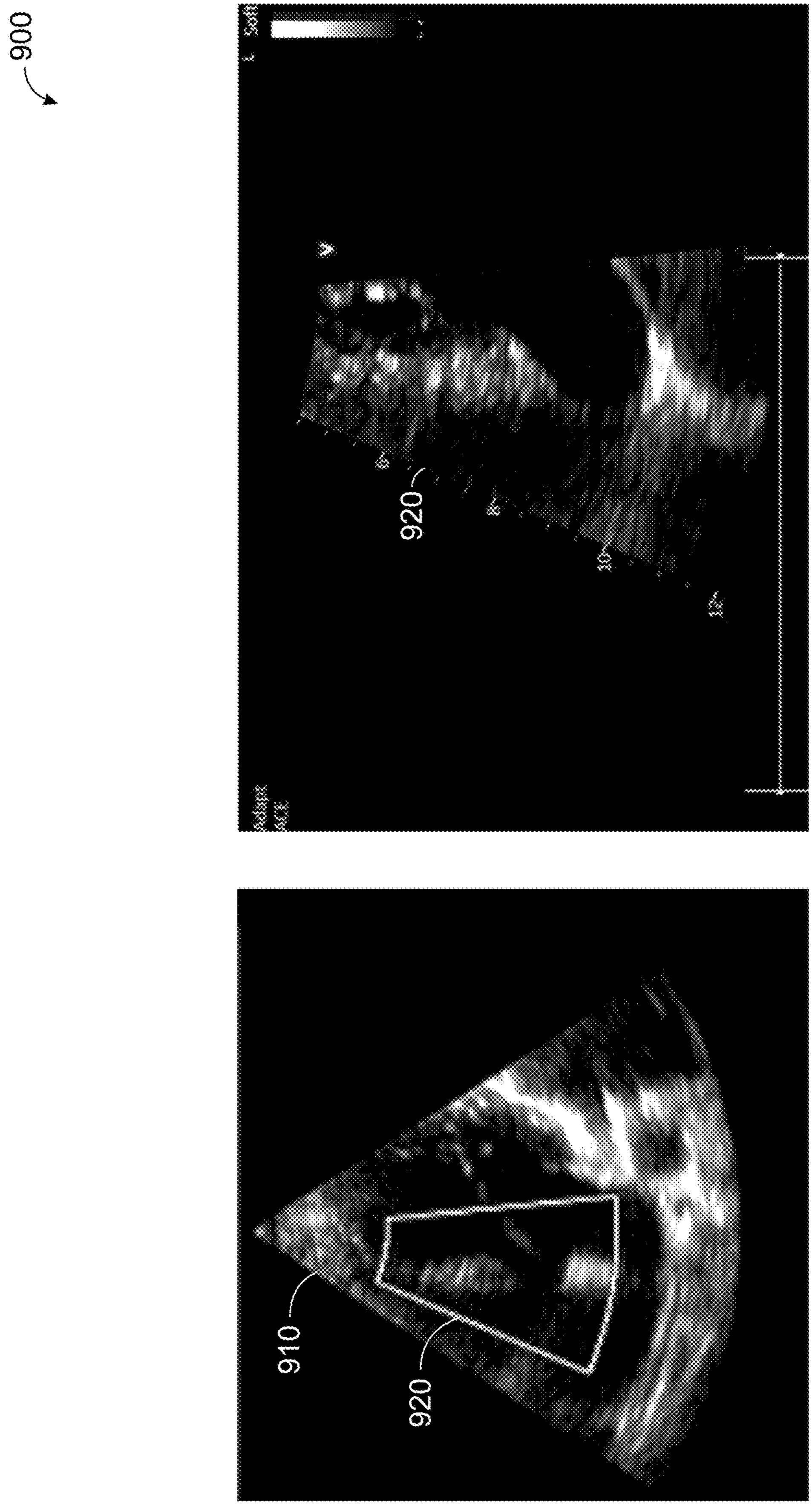
FIG. 9 is a diagram of an example region of interest and a subset of the region of interest.

FIG. 9 is a diagram of an example region of interest and a subset of the region of interest. As shown in FIG. 9, the strain imaging system 110 may acquire ultrasound data of a region of interest which corresponds to a chamber of the heart of a subject. The region of interest of the heart of the subject includes a first subset 910 and a second subset 920. The first subset 910 corresponds to a portion of the chamber and may be associated with relatively less motion over the cardiac cycle, whereas the second subset 920 corresponds to a specific portion of the chamber and may be associated with relatively more motion over the cardiac cycle. The strain imaging system 110 may acquire first ultrasound data of the region of interest of the heart of a subject at a first frame rate during a first cardiac cycle of the heart of the subject. For example, the strain imaging system 110 may acquire first ultrasound data that depicts the first subset 910 and the second subset 920 during the first cardiac cycle of the heart of the subject. As an example, the first frame rate may be fifty frames per second. The strain imaging system 110 may acquire second ultrasound data of a subset of the region of interest of the heart of the subject at a second frame rate during a second cardiac cycle of the heart of the subject. For example, the strain imaging system 110 may acquire second ultrasound data that depicts the second subset 920 and that does not depict the first subset 910. As an example, the second frame rate may be one hundred and fifty frames per second. In this way, the second ultrasound data is zoomed-in on the second subset 920, and may be acquired at a greater frame rate than as compared to the acquisition of the first ultrasound data in order to capture the increased motion of the second subset 920.

Figure 10A:
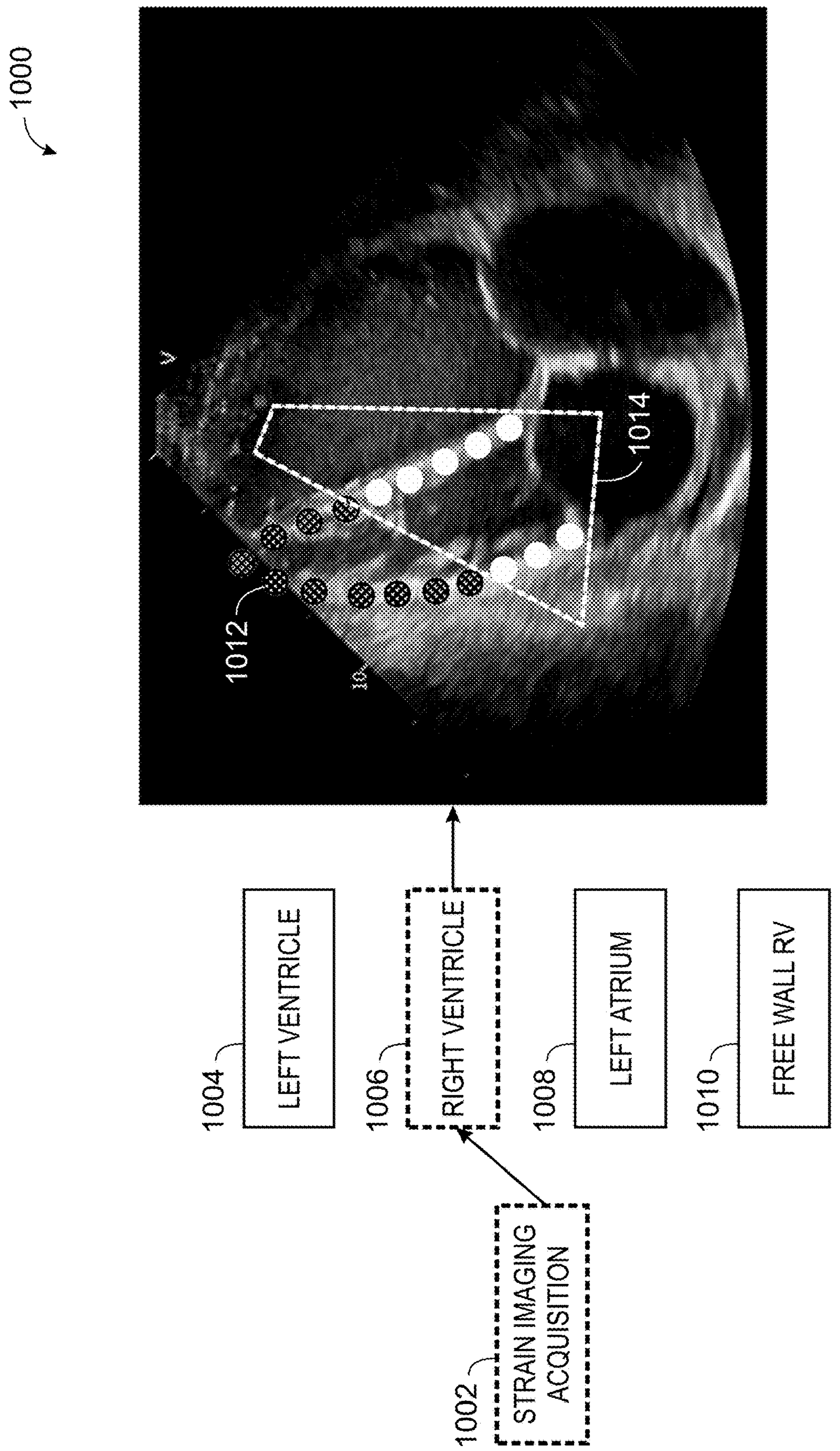
FIGS. 10A-10C are diagrams of example user inputs for acquiring ultrasound data corresponding to various subsets of a region of interest.
Figure 10B:
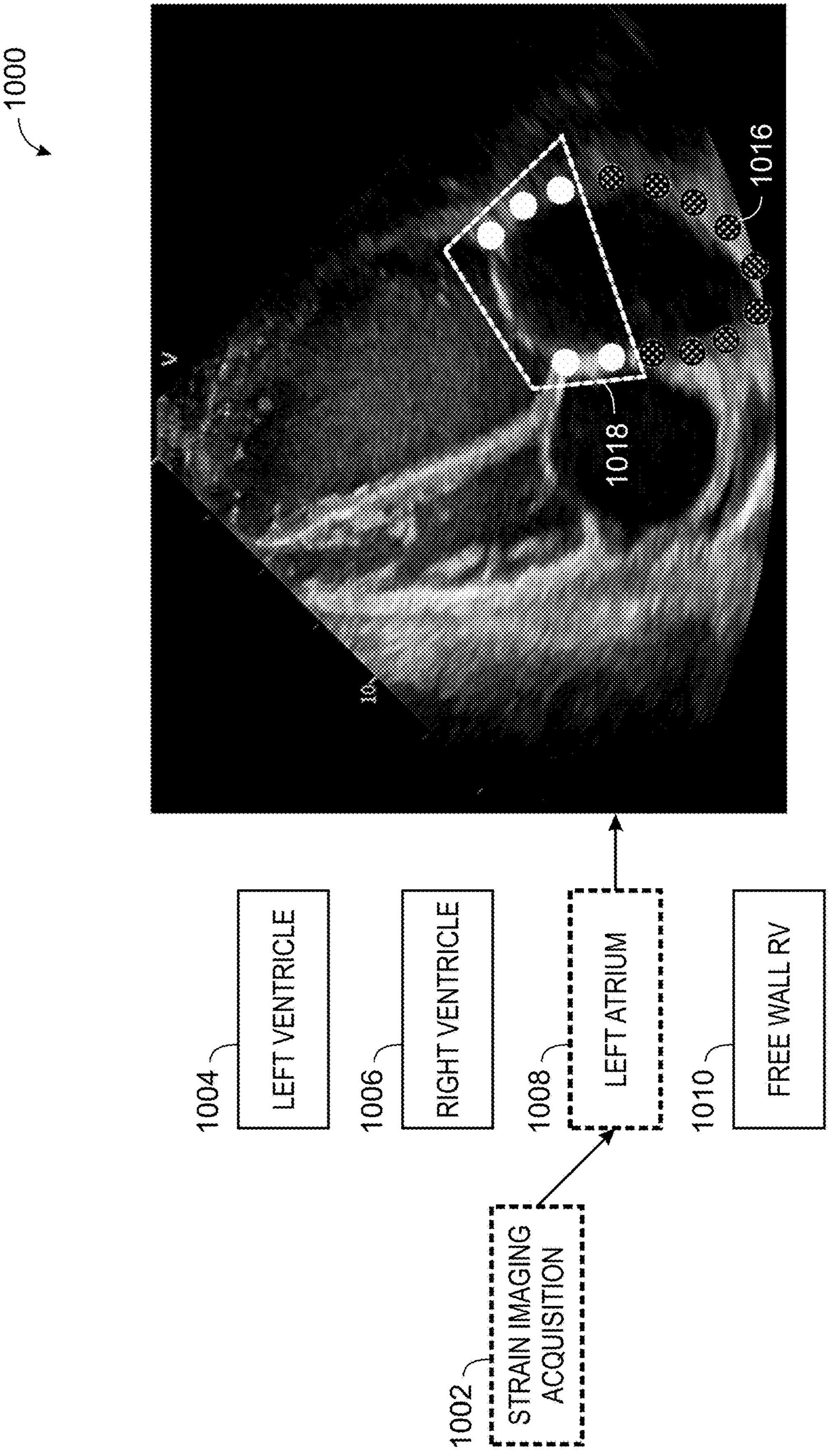
Figure 10C:
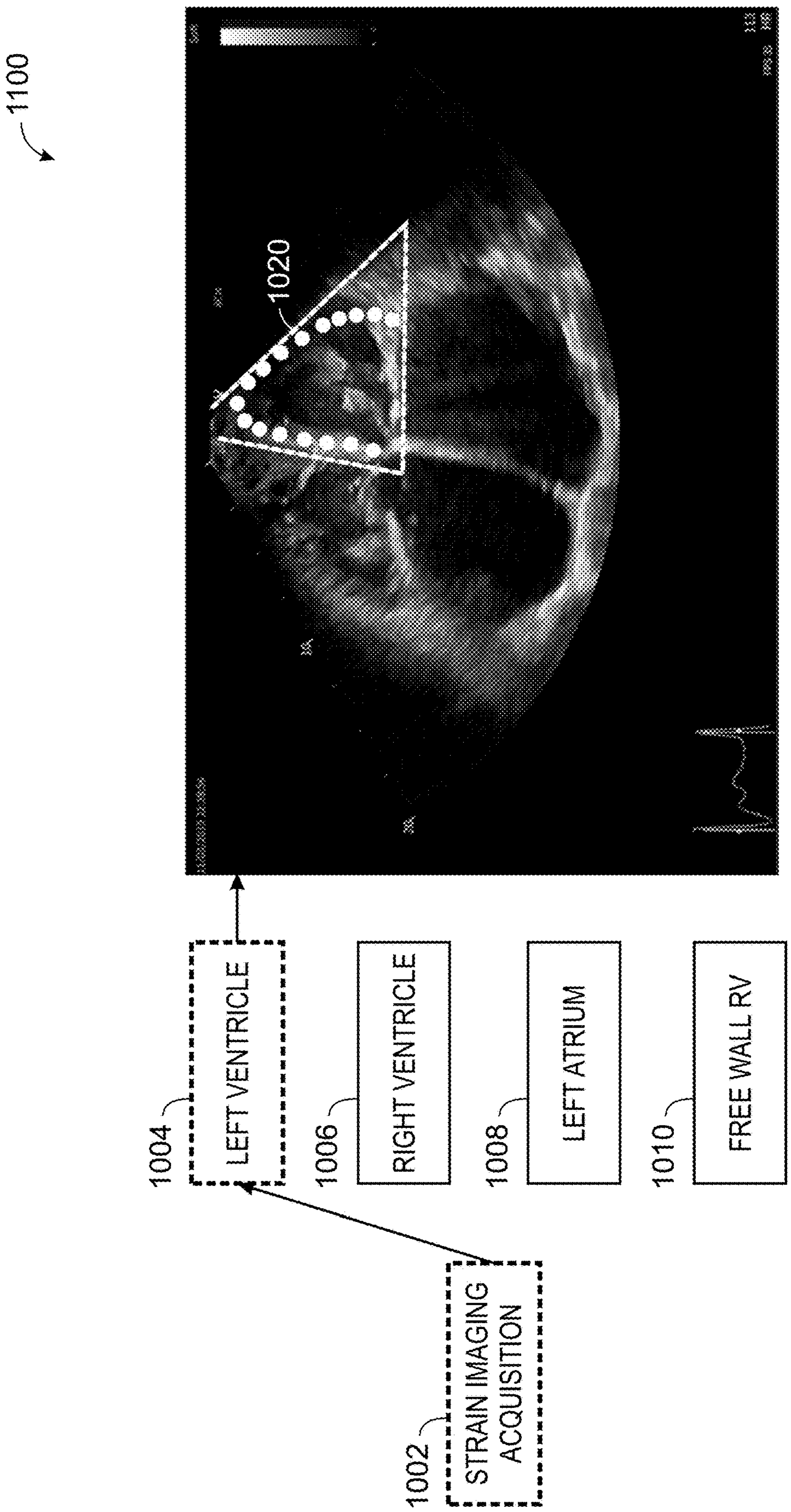

FIGS. 10A-10C are diagrams 1000 of example user inputs for acquiring ultrasound data corresponding to various subsets of a region of interest. As shown in FIGS. 10A-1C, a user interface of the strain imaging system 110 may display a user interface element 1002 corresponding to "strain imaging acquisition" which, when selected by the user, causes the strain imaging system 110 to perform strain imaging. As further shown in FIG. 10A, the user interface may display user interface elements corresponding to various regions of interest for performing the strain imaging. For example, the user interface may display a user interface element 1004 corresponding to "left ventricle," a user interface element 1006 corresponding to "right ventricle," a user interface element 1008 corresponding to "left atrium," a user interface element 1010 corresponding to "free wall RV," etc. Based on a user selection of a particular user interface element corresponding to a particular region of interest, the strain imaging system 110 may acquire ultrasound data corresponding to the region of interest to perform strain imaging.

As shown in FIG. 10A, the strain imaging system 110 may receive a user input that selects the user interface element 1006 corresponding to "right ventricle." In this case, the strain imaging system 110 may set the region of interest as the right ventricle, and acquire ultrasound data corresponding to the right ventricle for strain imaging. The strain imaging system 110 may acquire first ultrasound data of the right ventricle during a first cardiac cycle, segment the right ventricle of the heart into a set of myocardial segments, and track the respective segments during the first cardiac cycle using the first ultrasound data. Further, the strain imaging system 110 may determine motion characteristics of each of the myocardial segments, and determine a subset of the region of interest for which to acquire second ultrasound data based on the motion characteristics. For example, as shown, the strain imaging system 110 may determine a first subset 1012 and a second subset 1014. The first subset 1012 may be associated with relatively less motion than as compared to the second subset 1014. The strain imaging system 110 may acquire second ultrasound data of a subset of the region of interest of the heart of the subject at a second frame rate during a second cardiac cycle of the heart of the subject. For example, the strain imaging system 110 may acquire second ultrasound data that depicts the second subset 1014 and that does not depict the first subset 1012. In this way, the second ultrasound data is zoomed-in on the second subset 1014, and may be acquired at a greater frame rate than as compared to the acquisition of the first ultrasound data in order to capture the increased motion of the second subset 1014. The strain imaging system 110 may perform strain imaging using the first ultrasound data and the second ultrasound data, and determine information related to cardiac deformation of the right ventricle of the heart of the subject using strain imaging, the first ultrasound data, and the second ultrasound data.

As shown in FIG. 10B, the strain imaging system 110 may receive a user input that selects the user interface element 1008 corresponding to "left atrium." In this case, the strain imaging system 110 may set the region of interest as the left atrium, and acquire ultrasound data corresponding to the left atrium for strain imaging. The strain imaging system 110 may acquire first ultrasound data of the left atrium during a first cardiac cycle, segment the left atrium of the heart into a set of myocardial segments, and track the respective segments during the first cardiac cycle using the first ultrasound data. Further, the strain imaging system 110 may determine motion characteristics of each of the myocardial segments, and determine a subset of the region of interest for which to acquire second ultrasound data based on the motion characteristics. For example, as shown, the strain imaging system 110 may determine a first subset 1016 and a second subset 1018. The first subset 1016 may be associated with relatively less motion than as compared to the second subset 1018. The strain imaging system 110 may acquire second ultrasound data of a subset of the region of interest of the heart of the subject at a second frame rate during a second cardiac cycle of the heart of the subject. For example, the strain imaging system 110 may acquire second ultrasound data that depicts the second subset 1018 and that does not depict the first subset 1016. In this way, the second ultrasound data is zoomed-in on the second subset 1018, and may be acquired at a greater frame rate than as compared to the acquisition of the first ultrasound data in order to capture the increased motion of the second subset 1018. The zoomed acquisition reduces both the depth and width of the ultrasound image acquisition, which may lead to a considerable increase in temporal resolution. The strain imaging system 110 may perform strain imaging using the first ultrasound data and the second ultrasound data, and determine information related to cardiac deformation of the left atrium of the heart of the subject using strain imaging, the first ultrasound data, and the second ultrasound data.

As shown in FIG. 10C, the strain imaging system 110 may receive a user input that selects the user interface element 1004 corresponding to "left ventricle." In this case, the strain imaging system 110 may set the region of interest as the left ventricle, and acquire ultrasound data corresponding to the left ventricle for strain imaging. The strain imaging system 110 may acquire first ultrasound data of the left ventricle during a first cardiac cycle, segment the left atrium of the heart into a set of myocardial segments, and track the respective segments during the first cardiac cycle using the first ultrasound data. Further, the strain imaging system 110 may determine motion characteristics of each of the myocardial segments, and determine a subset of the region of interest for which to acquire second ultrasound data based on the motion characteristics. Here, as shown, the strain imaging system 110 may determine a subset 1020 that corresponds to the entire region of interest. The strain imaging system 110 may acquire second ultrasound data of a subset of the region of interest of the heart of the subject at a second frame rate during a second cardiac cycle of the heart of the subject. For example, the strain imaging system 110 may acquire second ultrasound data that depicts the subset 1020. In this way, the second ultrasound data is zoomed-in on the subset 1020, and may be acquired at a greater frame rate than as compared to the acquisition of the first ultrasound data in order to capture the increased motion of the subset 1020. The strain imaging system 110 may perform strain imaging using the first ultrasound data and the second ultrasound data, and determine information related to cardiac deformation of the left ventricle of the heart of the subject using strain imaging, the first ultrasound data, and the second ultrasound data. The zoomed area of the second cardiac cycle may potentially cover the entire segmented region of interest. As particular, the depth may be 20 centimeters, the frame rate may be 35 frames per second, and the heart rate may be 113 beats per minute. By zooming around the subset 1020 (which reduces depth and width), the frame rate may significantly increase for this high heart rate scan.

According to an embodiment, since the frame rate for the basal segments is higher than mid to apical segments, the granularity of the motion is higher at the base. However, since the motions in apical segments are small, the strain imaging system 110 may assume a linearized motion to fill in the motion for unavailable timestamps.

According to an embodiment, there might be motion discontinuities across zoomed region of interest boundaries. Therefore, the strain imaging system 110 may apply motion regularization to generate smooth motion transitions across the boundaries.

According to an embodiment, the strain imaging system 110 may detect movement of the ultrasound probe 302 and/or the subject from the first cardiac cycle to the second cardiac cycle. For example, the strain imaging system 110 may detect movement of the ultrasound probe 302 and/or the subject from the first cardiac cycle to the second cardiac cycle by comparing the corresponding data that are available at both cardiac cycles at the same timestamps. The corresponding data may be valve hinge points, or the like. The strain imaging system 110 may compensate for the motion and remove the motion from the estimated displacements.

According to an embedment, the strain imaging system 110 may detect heart rate variability, and select cardiac cycles with minimum length differences.

The present disclosure enhances strain imaging in subjects with high heart rates. This improvement may be achieved by addressing temporal undersampling issues of echo scans near rapidly moving structures through the implementation of a mixed full and zoomed acquisition. The present disclosure eliminates, or reduces, the need for users to manage acquisition frame rates during a scan when performing strain imaging using ultrasound. If the frame rate is below a threshold, the strain imaging system 110 may rejects the ultrasound data for calculating strain. By enhancing the accuracy of strain imaging and minimizing user interaction time, the present disclosure significantly reduces the time required for strain imaging and improves accuracy of strain imaging in assessing subjects with high heart rates.

According to an embodiment, the strain imaging system 110 may use one or more AI models. The one or more AI models may be associated with a training phase, a deployment phase, and a monitoring phase. In the training phase, the strain imaging system 110 may receive and process training data to generate a trained model. The training data may be generated, received, or otherwise obtained from internal and/or external resources.

Generally, the trained model may include a set of variables (e.g., nodes, neurons, filters, or the like) that are tuned (e.g., weighted, biased, or the like) to different values via the application of the training data. According to an embodiment, the training process may employ supervised, unsupervised, semi-supervised, and/or reinforcement learning processes to train the model. According to an embodiment, a portion of the training data may be withheld during training and/or used to validate the trained model.

For supervised learning processes, the training data may include labels or scores that may facilitate the training process by providing a ground truth. For example, the labels or scores may indicate an output of the model. Training may proceed by feeding a training dataset including the training data into the model. The model may have variables set at initialized values (e.g., at random, based on Gaussian noise, based on pre-trained values, or the like). The model may generate an output based on the training dataset being input to the model. The output may be compared with the corresponding label or score (e.g., the ground truth) indicating the known output, which may then be back-propagated through the model to adjust the values of the variables. This process may be repeated for a plurality of samples at least until a determined loss or error is below a predefined threshold. According to an embodiment, some of the training data may be withheld and used to further validate or test the trained model.

For unsupervised learning processes, the training data may not include pre-assigned labels or scores to aid the learning process. Instead, unsupervised learning processes may include clustering, classification, or the like, to identify naturally occurring patterns in the training data. As an example, the training data may be clustered into groups based on identified similarities and/or patterns. K-means clustering or K-Nearest Neighbors may also be used, which may be supervised or unsupervised. Combinations of K-Nearest Neighbors and an unsupervised cluster technique may also be used. For semi-supervised learning, a combination of training data with pre-assigned labels or scores and training data without pre-assigned labels or scores may be used to train the model.

When reinforcement learning is employed, an agent (e.g., an algorithm) may be trained to make a decision from the training data through trial and error. For example, based on making a decision, the agent may then receive feedback (e.g., a positive reward if the prediction was above a predetermined threshold), adjust its next decision to maximize the reward, and repeat until a loss function is optimized.

After being trained, the trained model may be stored and subsequently applied by the strain imaging system 110 during the deployment phase. For example, during the deployment phase, the trained model executed by the strain imaging system 110 may receive input data. During the deployment phase, the trained model may perform one or more operations as described in connection with FIG. 5.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. A system comprising:

a memory configured to store instructions; and one or more processors configured to execute the instructions to:

acquire first ultrasound data of a region of interest of a heart of a subject at a first frame rate during a first cardiac cycle of the heart of the subject;

segment the region of interest of the heart into a set of myocardial segments;

track the set of myocardial segments during the first cardiac cycle;

determine motion characteristics of the set of myocardial segments;

determine the subset of the region of interest for which to acquire the second ultrasound data based on the motion characteristics;

acquire second ultrasound data of the subset of the region of interest of the heart of the subject at a second frame rate during a second cardiac cycle of the heart of the subject based on determining the subset of the region of interest for which to acquire the second ultrasound data;

perform strain imaging using the first ultrasound data and the second ultrasound data;

determine information related to cardiac deformation of the region of interest of the heart of the subject based on performing the strain imaging; and display the information related to cardiac deformation of the region of interest of the heart of the subject.

2. The system of claim 1, wherein the one or more processors are further configured to:

determine the subset of the region of interest of the heart of the subject for which to acquire the second ultrasound data based on predetermined information that delineates the subset of the region of interest.

3. The system of claim 1, wherein the one or more processors are further configured to:

generate an aggregated ultrasound data set based on the first ultrasound data and the second ultrasound data; and determine the information related to cardiac deformation of the region of interest of the heart of the subject using the aggregated ultrasound data set.

4. The system of claim 1, wherein the first ultrasound data depicts an entirety of the region of interest, and wherein the second ultrasound data does not depict the entirety of the region of interest.

5. The system of claim 1, wherein the one or more processors are further configured to:

receive a user input that selects a user interface element corresponding to the region of interest.

6. The system of claim 1, wherein the second frame rate is greater than the first frame rate.

7. A method comprising:

acquiring first ultrasound data of a region of interest of a heart of a subject at a first frame rate during a first cardiac cycle of the heart of the subject;

segmenting the region of interest of the heart into a set of myocardial segments;

tracking the set of myocardial segments during the first cardiac cycle;

determining motion characteristics of the set of myocardial segments;

determining the subset of the region of interest for which to acquire the second ultrasound data based on the motion characteristics;

acquiring second ultrasound data of the subset of the region of interest of the heart of the subject at a second frame rate during a second cardiac cycle of the heart of the subject based on determining the subset of the region of interest for which to acquire the second ultrasound data;

performing strain imaging using the first ultrasound data and the second ultrasound data;

determining information related to cardiac deformation of the region of interest of the heart of the subject based on performing the strain imaging; and displaying the information related to cardiac deformation of the region of interest of the heart of the subject.

8. The method of claim 7, further comprising:

determining the subset of the region of interest of the heart of the subject for which to acquire the second ultrasound data based on predetermined information that delineates the subset of the region of interest.

9. The method of claim 7, further comprising:

generating an aggregated ultrasound data set based on the first ultrasound data and the second ultrasound data; and determining the information related to cardiac deformation of the region of interest of the heart of the subject using the aggregated ultrasound data set.

10. The method of claim 7, wherein the first ultrasound data depicts an entirety of the region of interest, and wherein the second ultrasound data does not depict the entirety of the region of interest.

11. The method of claim 7, further comprising:

receiving a user input that selects a user interface element corresponding to the region of interest.

12. The method of claim 7, wherein the second frame rate is greater than the first frame rate.

13. A non-transitory computer-readable medium storing instructions that, when executed by one or more processors, cause the one or more processors to:

acquire first ultrasound data of a region of interest of a heart of a subject at a first frame rate during a first cardiac cycle of the heart of the subject;

segment the region of interest of the heart into a set of myocardial segments;

track the set of myocardial segments during the first cardiac cycle;

determine motion characteristics of the set of myocardial segments;

determine the subset of the region of interest for which to acquire the second ultrasound data based on the motion characteristics;

acquire second ultrasound data of the subset of the region of interest of the heart of the subject at a second frame rate during a second cardiac cycle of the heart of the subject based on determining the subset of the region of interest for which to acquire the second ultrasound data;

perform strain imaging using the first ultrasound data and the second ultrasound data;

determine information related to cardiac deformation of the region of interest of the heart of the subject based on performing the strain imaging; and display the information related to cardiac deformation of the region of interest of the heart of the subject.

14. The non-transitory computer-readable medium of claim 13, wherein the instructions further cause the one or more processors to:

determine the subset of the region of interest of the heart of the subject for which to acquire the second ultrasound data based on predetermined information that delineates the subset of the region of interest.

15. The non-transitory computer-readable medium of claim 13, wherein the instructions further cause the one or more processors to:

generate an aggregated ultrasound data set based on the first ultrasound data and the second ultrasound data; and determine the information related to cardiac deformation of the region of interest of the heart of the subject using the aggregated ultrasound data.

16. The non-transitory computer-readable medium of claim 13, wherein the first ultrasound data depicts an entirety of the region of interest, and wherein the second ultrasound data does not depict the entirety of the region of interest.

17. The non-transitory computer-readable medium of claim 13, wherein the second frame rate is greater than the first frame rate.

* * * * *